United States Patent
Marchisio et al.

(10) Patent No.: US 9,358,105 B2
(45) Date of Patent: Jun. 7, 2016

(54) SUPPORT DEVICE FOR HEART VALVE PROSTHESES

(71) Applicant: Sorin Group Italia S.r.l., Milan (IT)

(72) Inventors: Andrea Marchisio, Ivrea (IT); Giovanni Rolando, Chivasso (IT); Paolo Gaschino, Castagneto Po (IT)

(73) Assignee: Sorin Group Italia S.r.l., Milan (IT)

( * ) Notice: Subject to any disclaimer, the term of this patent is extended or adjusted under 35 U.S.C. 154(b) by 0 days.

(21) Appl. No.: 13/835,593

(22) Filed: Mar. 15, 2013

(65) Prior Publication Data

US 2013/0268068 A1 Oct. 10, 2013

(30) Foreign Application Priority Data

Apr. 4, 2012 (EP) .................................... 12425070

(51) Int. Cl.
*A61F 2/24* (2006.01)
(52) U.S. Cl.
CPC ............. *A61F 2/2412* (2013.01); *A61F 2/2427* (2013.01)
(58) Field of Classification Search
CPC ....... A61F 2/24; A61F 2/2496; A61F 2/2412; A61F 2/2415; A61F 2/2418; A61F 2/2427; A61B 2017/22097; A61B 2018/00369
USPC .............. 623/1.11, 2.11, 2.17, 2.18; 606/108, 606/127, 191
See application file for complete search history.

(56) References Cited

U.S. PATENT DOCUMENTS

| | | | |
|---|---|---|---|
| 5,443,502 A | | 8/1995 | Caudillo et al. |
| 5,713,953 A | | 2/1998 | Vallana et al. |
| 5,855,602 A | * | 1/1999 | Angell .......................... 623/2.11 |
| 2006/0084939 A1 | * | 4/2006 | Lentz ............................. 604/526 |
| 2008/0262603 A1 | | 10/2008 | Giaquinta et al. |
| 2009/0259303 A1 | * | 10/2009 | Elizondo et al. ................ 623/2.1 |
| 2010/0004739 A1 | * | 1/2010 | Vesely .......................... 623/2.11 |
| 2010/0161046 A1 | * | 6/2010 | Marquez et al. ............. 623/2.18 |
| 2011/0066232 A1 | * | 3/2011 | Riveron et al. .............. 623/2.11 |
| 2011/0098804 A1 | | 4/2011 | Yeung et al. |
| 2011/0276128 A1 | | 11/2011 | Cao et al. |

FOREIGN PATENT DOCUMENTS

| | | |
|---|---|---|
| EP | 0515324 B1 | 11/1992 |
| EP | 2387972 A1 | 11/2011 |
| WO | WO0064382 A2 | 11/2000 |

OTHER PUBLICATIONS

European Search Report issued in EP Application No. 12425070, mailed Jul. 5, 2012, 7 pages.
International Search Report and Written Opinion issued in PCT/IB2013/052080, mailed Jul. 31, 2013, 12 pages.
International Report on Patentability issued on PCT/IB2013/052080, Chapter 1, completed Oct. 7, 2014, 8 pages.

* cited by examiner

*Primary Examiner* — Christopher D Prone
*Assistant Examiner* — Rokhaya Diop
(74) *Attorney, Agent, or Firm* — Faegre Baker Daniels LLP

(57) ABSTRACT

A support device for implanting a stentless heart valve prosthesis having three leaflets adapted for coapting and defining three corresponding commissures is disclosed. The support device includes a shaft defining a manipulation axis, the shaft having a proximal portion and a distal portion, and three support formations integrally formed and extending from the proximal end of the shaft, the support formations angularly distributed about the manipulation axis of the shaft, such that each of the support formations correspond to locations of each of the commissures of the stentless heart valve prosthesis. The shaft includes a connection portion flexibly connecting the shaft and the support formations to permit a displacement of the manipulation axis with respect to the support formations. The shaft, the plurality of support formations and the connection portion are integrally formed from a single tubular element.

18 Claims, 7 Drawing Sheets

SUPPORT DEVICE FOR HEART VALVE PROSTHESES

CROSS-REFERENCE TO RELATED APPLICATION

This application claims priority to European Application No. 12425070.5 filed Apr. 4, 2012, which is herein incorporated by reference in its entirety.

TECHNICAL FIELD

This invention relates to cardiac valve prostheses and in particular to support devices therefor for assisting in the implantation of such devices.

BACKGROUND

Cardiac valve prostheses can essentially be divided into two basic categories, namely "mechanical" valve prostheses, in which the blood flow through the valve is controlled by one or more obturators constituted by rigid bodies mounted so as to be able to oscillate or tilt in a rigid support, and "biological" valve prostheses, in which blood flow is controlled by valve leaflets formed of biological tissue. The biological valve leaflet material, which is subject to treatment (stabilization) to render it biologically inert, can be derived from a natural cardiac valve taken from an animal (for example a pig) or can be formed from biological tissue other than valve tissue (for example, bovine pericardium). Biological valve prostheses may in turn take the form of "stented" valves, where the valve leaflets are mounted on a rigid or slightly flexible stent or armature, and "unstented," or "stentless," valves.

EP-A-0 515 324 and U.S. Pat. No. 5,713,953 disclose various embodiments of stentless cardiac valve prostheses, including embodiments where the biological material is replaced (either partially or completely) with an artificial/synthetic material such as a micro-porous and/or composite synthetic material, for example polyurethane. Stentless valve prostheses may exhibit as a whole characteristics of deformability that offer functional advantages due to a great similarity to the anatomy of natural valves. On the other hand, because stentless valves do no maintain a consistent shape, they may be somewhat more challenging to implant properly. Optimal implantation of a stentless valve, either by conventional or minimally-invasive surgical techniques, may involve positioning the prosthesis at the implantation site (e.g., an aortic site) using a holder device. Such a holder may support the prosthesis during production, packaging and/or implantation of the prosthesis by the surgeon. Holder devices may include a support or "grip" hub adapted for connection to a manipulation handle. The surgeon can thus locate a prosthesis (held by the holder) at the implantation site and properly orient it with respect to the native valve anatomy.

One such exemplary holder is shown in US 2008/0262603 A1, which includes a grip element and a plurality of arms for supporting a prosthetic heart valve at an intermediate position between the commissures. The holders shown in the prior art however are either quite complex in construction or design. Additionally, the manipulation capabilities of these holders may often be not completely satisfactory.

SUMMARY

The present invention, according to various embodiments, provides a support device for stentless heart valve prostheses, which is easy to manufacture and offers better manipulation performances compared to known devices. In various exemplary embodiments of the invention, these problems are solved by a support device for stentless valve prostheses having the features of the appended claims.

According to one embodiment, the problem is solved by a support device for a stentless heart valve prosthesis including: a shaft defining a manipulation axis, a plurality of support formations for a stentless valve prosthesis, a connection portion flexibly connecting the shaft and the support formations to permit a displacement of the manipulation axis with respect to the support formations, wherein the shaft, the plurality of support formations and the connection portion are formed in a single piece from a tubular element.

Additionally, preferred embodiments of the invention include, for example:

Embodiment 1: a support device for stentless heart valve including: a shaft defining a manipulation axis, a plurality of support formations for a stentless valve prosthesis, and a connection portion flexibly connecting the shaft and the support formations to permit a displacement of the manipulation axis with respect to the support formations, wherein the shaft, the plurality of support formations and the connection portion are formed in a single piece from a tubular element.

Embodiment 2: the support device of embodiment 1, wherein the tubular element is made of a shape memory material.

Embodiment 3: the support device of either embodiment 1 or 2, wherein the tubular element is made of nitinol.

Embodiment 4: the support device of any of the previous embodiments, wherein the plurality of support formations includes support arms which are cut in the tubular element and shaped so that they protrude there from, the support arms departing from a hub provided on the tubular element adjacent to the connection portion.

Embodiment 5: the support device of embodiment 4, wherein the support arms include a first portion extending radially away from the manipulation axis and a second portion, bent with respect to the first portion, which extends substantially parallel to the manipulation axis.

Embodiment 6: the support device of embodiment 5, wherein the first portion of each support arm also extends in an axial direction of the support device.

Embodiment 7: the support device of any of embodiments 4 to 6, including three support arms arranged with an even angular spacing around the manipulation axis.

Embodiment 8: the support device of any of the previous embodiments, wherein the connection portion consists of a helical track cut in the tubular element.

Embodiment 9: the support device of any of the previous claims, wherein the shaft comprises a free end at which connection formations configured for coupling the support device to a manipulation tool are provided.

Embodiment 10: the support device of any of embodiments 4 to 7, further including at least one through hole provided on the tubular member at a radial position corresponding to that of a supporting formation associated thereto.

Embodiment 11: the support device of embodiment 10, wherein the at least one through hole is provided on the hub.

Embodiment 12: the support device of embodiment 5, wherein each support arm includes a first eyelet located at a position between the first and second portions and a second eyelet at a free end of the second portion.

Embodiment 13: the support device of Embodiment 5 or Embodiment 10, further comprising at least one through hole located on the first portion of each supporting arm.

Embodiment 14: a combination of a stentless heart valve prosthesis and a support device according to any of embodiments 1 to 13.

Embodiment 15: the combination of embodiment 14, wherein the stentless heart valve prosthesis is an aortic valve prosthesis including three coapting valve leaflets and three commissures, each coupled to a corresponding support formation.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

The invention will now be described with reference to the attached figures, provided purely by way of non limiting example, and wherein.

Figure 1:
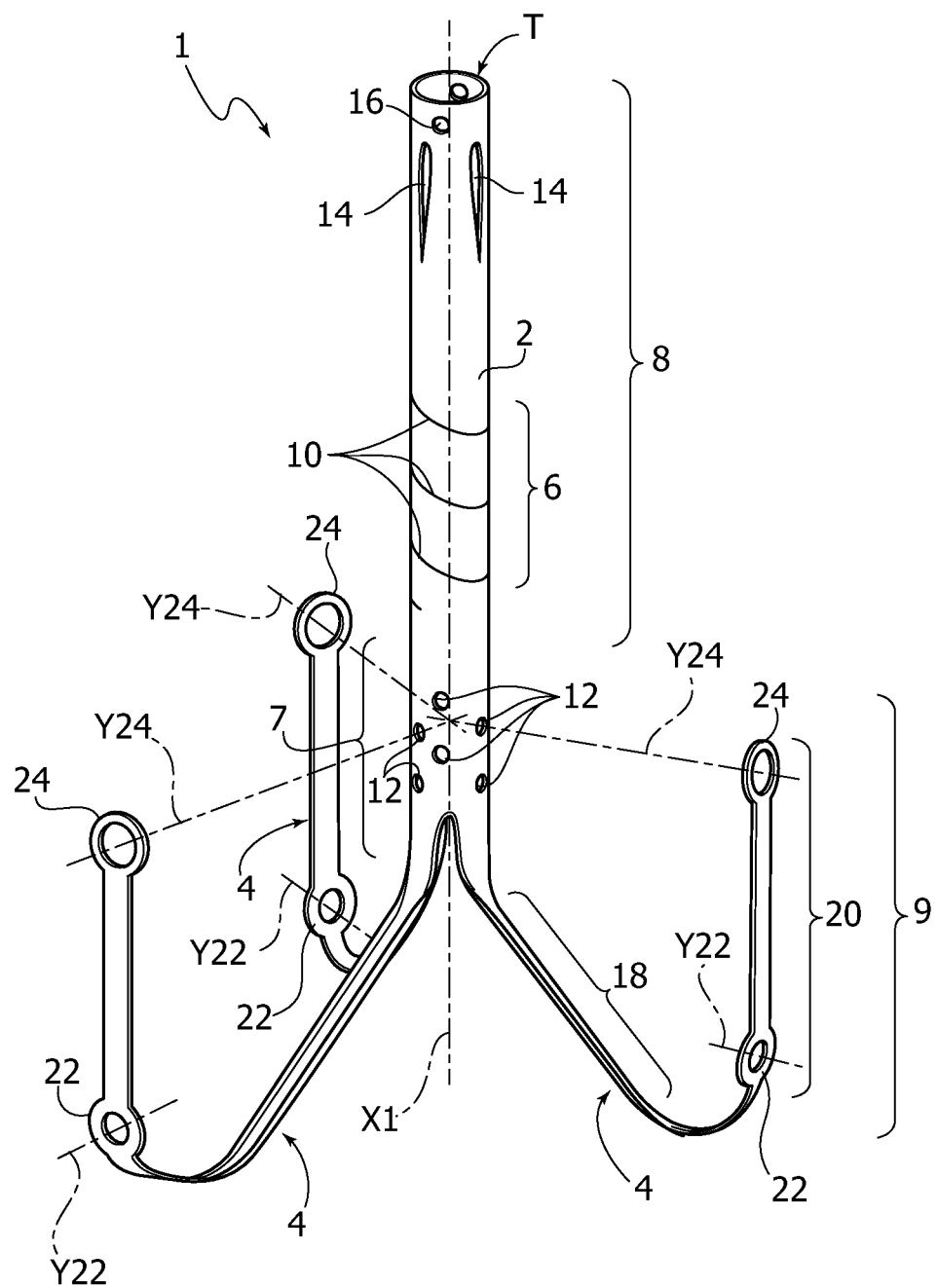
FIG. 1 is a perspective view of a support device for stentless heart valve prostheses according to various exemplary embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

In FIG. 1, reference number 1 identifies as a whole a supporting device for stentless heart valve prostheses according to various exemplary embodiments. The supporting device 1 includes a shaft 2 defining a manipulation axis X1, a plurality of support formations 4 intended for supporting a stentless heart valve prosthesis and a connection portion 6 flexibly connecting the shaft 2 and the supporting formations 4, which in turn depart form a hub 7 immediately adjacent to the connection portion 6. All the components mentioned above are formed in a single piece from a tubular element T which is subject to a number of cutting and forming operations. In various embodiments the tubular element T has a circular cross section.

In various embodiments, in a distal portion 8 of the tubular element T, the shaft 2 and the connection portion 6 include a helical track 10 cut into the tubular member T. In various embodiments, in a proximal portion 9 of the tubular element T, the hub 7 has a plurality of radial holes located thereon. In exemplary embodiments, such holes may be arranged in pairs oriented along the direction of the manipulation axis X1. In some embodiments, adjacent pairs of radial holes 12 may be axially staggered.

In the present description, the terms "distal" and "proximal" are used with reference, so to say, to the implantation site, i.e., proximal being a location close to the implantation site (and corresponding to that of a valve prosthesis coupled to the support device 1), while distal being a location away from the implantation site.

In various embodiments, on the distal portion 8, in particular at a free end of the shaft 2, there may be provided a number of coupling formations 14, 16, which may be in the form of longitudinal slits 14 or in the form of radial holes 16 or both. Such coupling formations are intended to provide a connection, e.g., of the snap-fit type, of the support device 1 to a manipulation tool which will be described in the following. In other embodiments, no such formations 14 and 16 are present, so that the coupling between the manipulation tool and the support device may be achieved by relying upon, e.g., an interference fit.

In various embodiments, on a second portion of the tubular element T the support formations 4 are cut and formed so that each supporting formation is shaped as a supporting arm including a first portion 18 extending radially away from the manipulation axis X1 and a second portion 20, which is bent with respect to the first portion 18 and which extends substantially parallel to the manipulation axis X1. In some embodiments, such as those depicted in the figures, the first portions 18 may be formed so to extend also axially away from the shaft 2.

Furthermore, in various embodiments, each supporting formation 4 may include a first eyelet 22 located at a position corresponding to that of the bend between the first portion 18 and the second portion 20 and a second eyelet 24 located at a free end of the second portion 20. In other embodiments, each supporting arm 4 may include only one eyelet, either being the eyelet 22 or 24. In various embodiments, the eyelets 22, 24 may be oriented so that respective axes Y22, Y24 thereof are incident to the manipulation axis X1.

Figure 2:
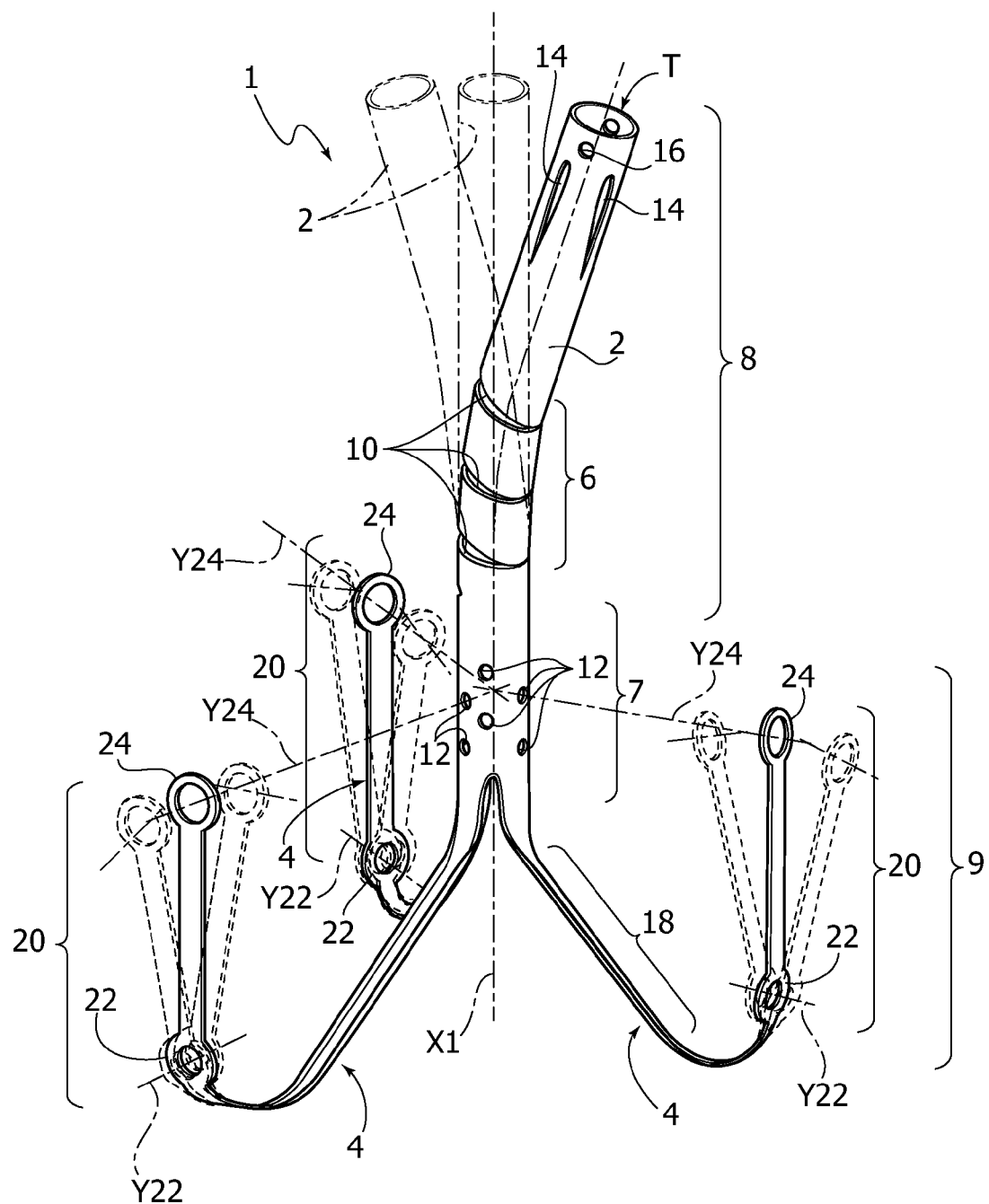
FIG. 2 is a perspective view corresponding to that of FIG. 1 but showing various deformed conditions.

As shown in the exemplary embodiment of FIG. 2, the supporting device 1 includes three supporting arms 4, which are disposed with even angular spacing (i.e., 120 degrees) around the manipulation axis X1. As shown, the supporting arms are capable of flexing inwards and outwards in a radial direction. FIG. 2 also shows, in phantom lines, two possible deformed conditions of each of the supporting arms 4.

In various embodiments, the deformation capabilities of each supporting arm 4 may be mainly concentrated on the second portion 20 thereof, while the first portions 18 may be designed with a greater bending stiffness to provide a sufficient support action to a valve prosthesis which is coupled to the device 1. By way of example, in one embodiment, the portions 18 may be shaped so to have a U-shaped cross section which offers a higher bending moment of inertia. According to various embodiments, the first portion 18 and the second portion 20 are configured (e.g., type of material, thickness, or cross-sectional configuration) such that the first portion 18 has a higher bending stiffness than the second portion 20.

In the various embodiments where the connecting portion 6 is a helical track 10 made (e.g., cut into) a stretch of the tubular element T, the connector portion 6 allows a displacement of the manipulation axis X1 with respect to the supporting formations 4. Such a displacement may be obtained by manipulating the shaft 2. As shown in certain figures, in exemplary embodiments, the helical track 10 extends around the tubular element three times (e.g., about 1080 degrees). In other embodiments, the helical track extends more or fewer times around the circumference of the tubular element T.

The helical track 10 breaks the structural continuity of the tubular element T at an intermediate position between the shaft 2 and the hub 7 from which the supporting arms 4 extend. This may be regarded as substantially equivalent, so to say, to provide a leaf, helically wound, spring connecting the shaft 2 and the hub 7 and being capable of providing an effect which resembles that of a universal joint. In particular, as shown in FIG. 2, a displacement of the manipulation axis X1 may be achieved by the deformation of the connection portion 6, wherein various "turns" of the spring-like element defined by the cutting of the helical track 10 are able to separate axially thereby allowing a departure from the rectilinear (i.e., straight) shape of the proximal portion 8.

Figure 3:
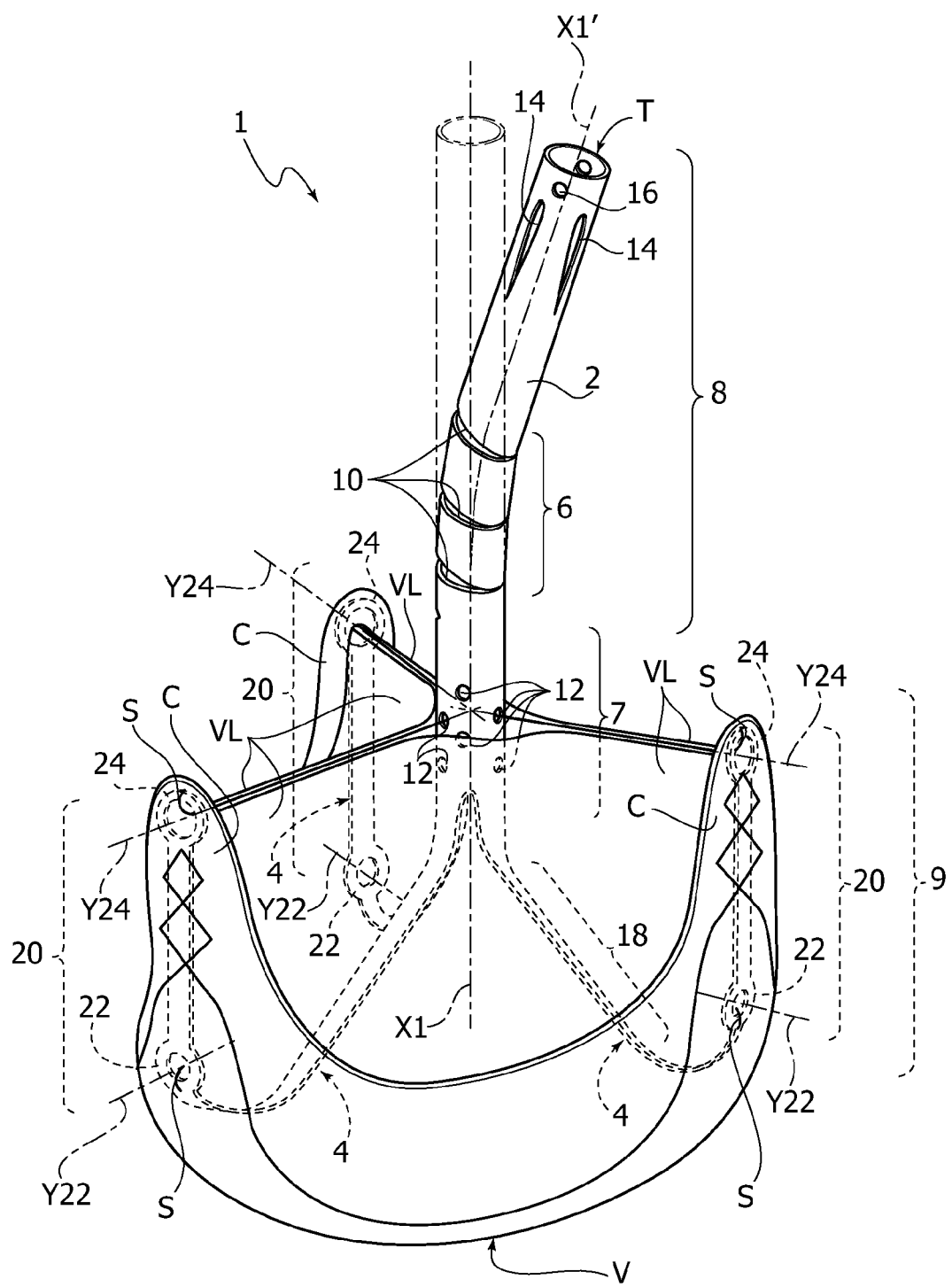
FIG. 3 is a perspective view of a support device according to various embodiments coupled to a biological stentless heart valve prosthesis and shown in one possible deformed condition.

FIG. 3 shows the supporting device 1, according to an exemplary embodiment, coupled to an exemplary stentless heart valve prosthesis. The stentless heart valve prosthesis is indicated by the reference V and includes, in one embodiment, three coapting valve leaflets VL defining three corresponding commissures C. As shown, the supporting arms 4 of the device 1, and in particular the portions 20 thereof, are located at or near the commissures C. As shown, the portions 20 are arranged within the orifice defined by the valve V, particularly inside the commissures C at a position substantially comprised between two adjacent leaflets VL.

Figure 7:
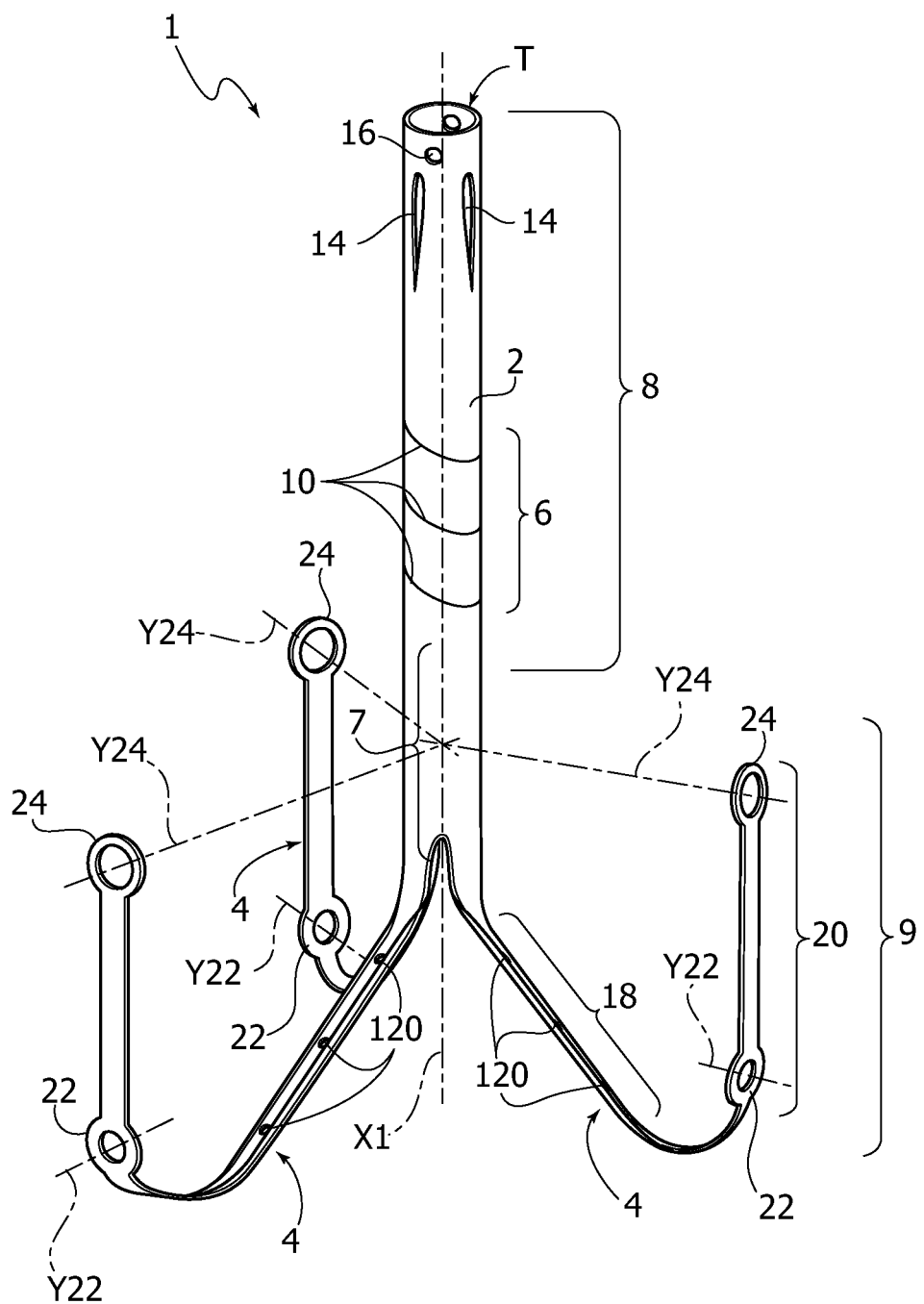

In various embodiments, the number of the supporting formations 4 may be chosen so as to be equal to the number of the commissures C of the valve V which is to be coupled to the support device 1. In various embodiments, the valve prosthesis V may be temporarily attached to the arms 4 by means of suture threads S piercing the commissures C and routed through corresponding eyelets 22, 24. Each suture thread may then be passed through the holes 12 (or, more generally, may be routed through the hub 7) in order to provide a safe anchoring of the valve prosthesis V to the support device 1. Alternatively, in some embodiments such as those depicted in FIG. 7, at least one through hole 120, and preferably more than one, may be formed on the portion 18 of each of the supporting arms 4, so that the suture threads S may be routed therethrough. In other embodiments, both the holes 12 on the hub 7 and the holes 120 on the portions 18 of the arms 4 are present. In such embodiments, the suture threads may be passed through either the holes 12 or 120, or even both, depending e.g. on specific requests of the practitioner.

Figure 4:
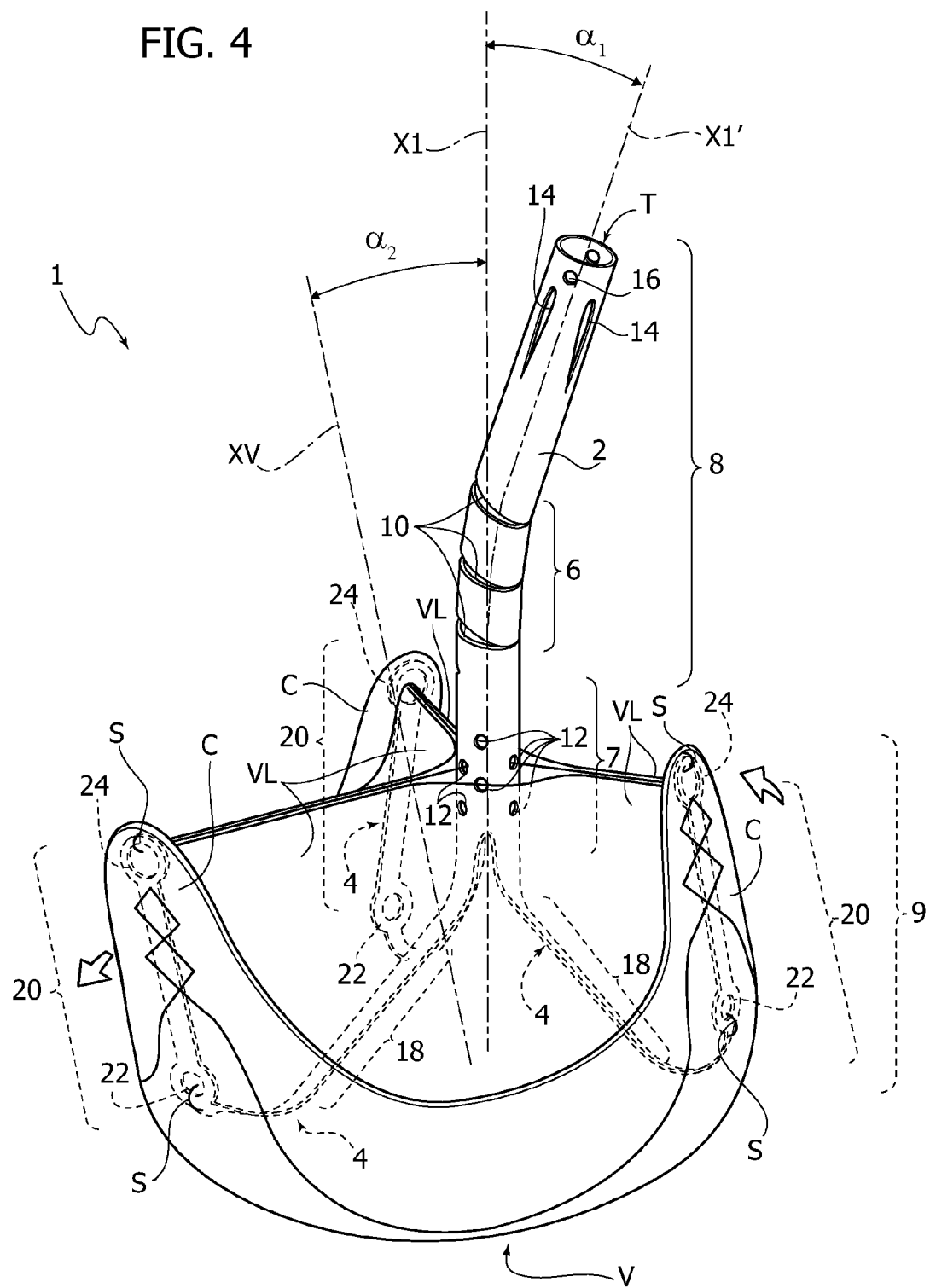
FIG. 4 is a perspective view of a support device according to various embodiments coupled to a biological stentless heart valve prosthesis and shown in another possible deformed condition.

As shown in FIG. 4, in various embodiments, the bending capabilities of each of the supporting arms 4 allows for a multiple displacement within the support device 1. For example, in addition to the displacement of the shaft 2 with respect to the supporting formations 4, that is the displacement of the manipulation axis X1 by an angle $\alpha_1$ with respect to its non-displaced position, an additional displacement may be achieved between the manipulation axis X1 and a main axis XV of the valve prosthesis V. The manipulation axis is identified by the reference X1 in its non-displaced position and by the reference X1' in its displaced position. This may be achieved because, with reference to FIG. 4, an angle $\alpha_2$ by which the axis XV may be inclined with respect to the manipulation axis X1 may be the result of the bending of each of the supporting arms 4, in particular of the portions 20.

Figure 5:
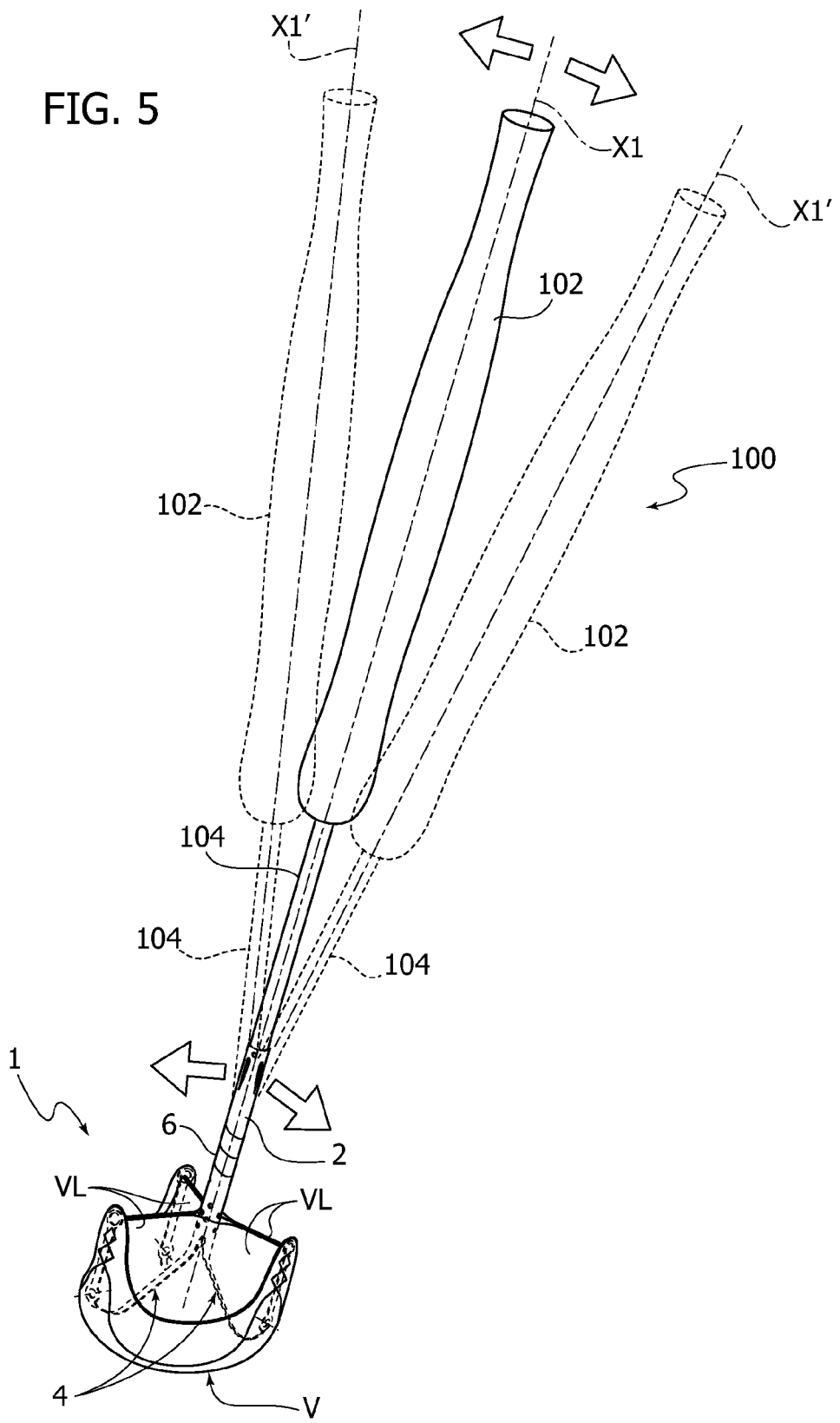
FIG. 5 is a perspective view of an example of a manipulation tool which can be coupled to a support device according to various embodiments of the invention.

As shown in FIG. 5, a manipulation tool 100 may be coupled to the support device 1. The manipulation tool 100 may comprise, in various embodiments, a handle 102 which may be designed with an ergonomical shape, and a rod 104 which is sized and dimensioned to fit into the shaft 2 and engage in corresponding ones of the connection formations 14, 16. In embodiments wherein no such formations 14, 16 are present, the rod 104 is sized and dimensioned so to provide an interference with the tubular element T, so that a coupling by means of an interference fit between the rod 104 and the support device 1 (in particular the shaft 2) can be achieved.

For performing the implantation of the valve V, the practitioner may thus vary the position of the manipulation axis X1 with respect to its nominal (i.e., non-displaced) position and also achieve a displacement of the valve axis XV with respect to the axis X1 depending on the specific needs during the intervention. For example, apart from ensuring a correct positioning of the valve V with respect to the implantation site (in the embodiments herein depicted, reference is made to an aortic implantation site, since the valve V shown in the figures is an aortic valve prosthesis) the practitioner may also displace the support device 1 with respect to the valve V in order to better perform, for example, stitching operations in a specific region of the valve V. After having reached the implantation site, for example with a retrograde approach, should the combination of the manipulation tool 100 and the support device 1 be of hindrance for the practitioner when stitching the valve V to the implantation site, the practitioner may displace the shaft 2 and the valve V with respect to the manipulation axis X1 to clear the way for performing such operations.

When the prosthesis V is firmly anchored to the implantation site, the practitioner may then cut the suture threads S and separate the support device 1 from the prosthesis V by gently pulling the device 1 axially away from the prosthesis V.

In various embodiments, the support device 1 lends itself to various structural modifications. For example, in some embodiments, the connection portion 6 may be provided as a weakened stretch on the tubular element T defined by a plurality of axial slits resulting in the shaft 2 and the hub 7 being connected by a plurality of bridging elements capable of buckling inwards (and outwards) towards the axis X1 in order to provide the desired degree of deformation. Moreover, in various embodiments, each pair of holes 12 may be replaced by a single hole, or in alternative, a hook obtained by cutting the corresponding, unfolded shape thereof into the tubular element T and then bending the cut shape outwards of the tubular element T or, as a further alternative, by C-shaped openings.

In various embodiment, it is preferred that the material of the tubular element be a shape memory material such as a super elastic alloy. According to various exemplary embodiments, the tubular element is made of Nitinol. When Nitinol is employed, the support device 1 may be cut by using the same techniques as those used for cutting stents, e.g., the various components of the support device 1 may be cut into the tubular element T by means of laser beams. In various embodiments, the structure itself of the support device 1 may be subjected to a large number of modifications and various other structures, shapes, patterns may be conferred to each of the components thereof (including the connection portion 6, the shaft 2, the hub 7 and the supporting formations 4) by varying the cutting path of the laser beam which are used to cut the tube T.

Figure 6:
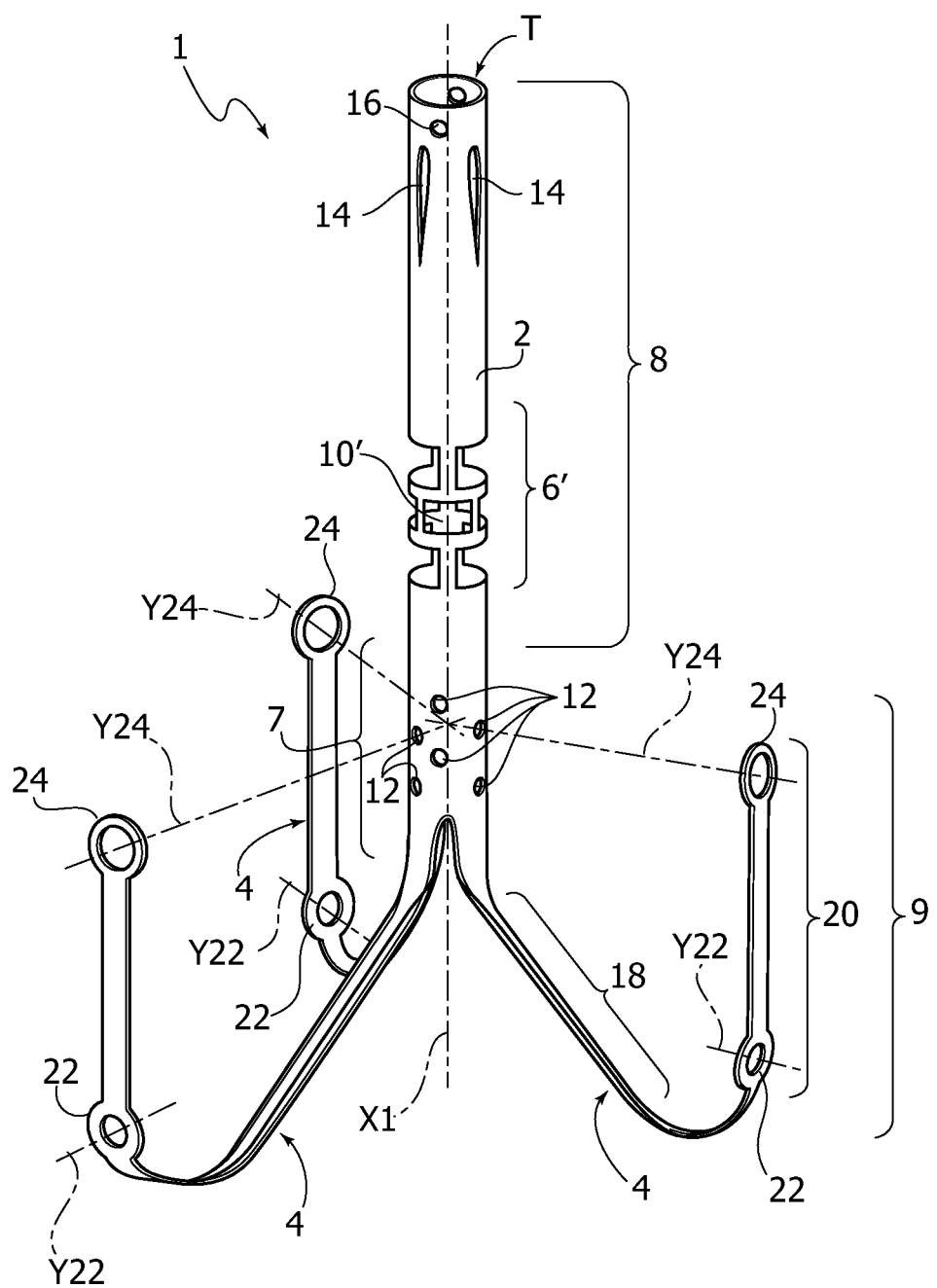
FIGS. 6 and 7 are perspective views showing further exemplary embodiments of the support device for stentless heart valve prostheses.

As shown in FIG. 6, in exemplary embodiments, the connection portion 6' may be provided as an apertured structure. For example, the connection portion 6' may be a stent-like structure including a plurality of apertures 10' cut into the shaft 2. In such embodiments, the apertures may for example have a rectangular shape and may be arranged in radially offset bands. The connection portion 6 may moreover be provided in combination with either arrangement of the holes 12 and/or 120 described above. In various exemplary embodiments, the connection portion 6 is provided as an apertured structure and the holes 12 and/or the holes 120 are present.

Without prejudice to the underlying principles of the invention, the details and embodiments may vary, even significantly, with respect to what has been described herein, merely by way of example, without departing from the scope of the invention as defined by the annexed claims. Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A support device for implantation of a stentless aortic heart valve prosthesis having three leaflets adapted for coapting and defining three corresponding commissures, the support device including:
 a shaft defining a manipulation axis, the shaft having a distal portion and a proximal portion having a coupling formation adapted for coupling with a manipulation tool; and
 three support formations integrally formed and extending from the distal portion of the shaft, the support formations disposed with even angular spacing around the manipulation axis of the shaft, such that each of the support formations correspond to locations of each of the commissures of the stentless heart valve prosthesis;
 wherein each of the support formations includes a first portion, the first portion of each support arm extends distally away from the shaft and radially away from the manipulation axis and a second portion of each support arm is bent with respect to the first portion and extends proximally and parallel to the manipulation axis, the first portion having a longitudinal length and a first cross-sectional configuration along the longitudinal length, and a second portion, having a second cross-sectional configuration, and extending from the first portion, the first cross-sectional configuration along the longitudinal length of the first portion having a U-shape and configured such that the first portion has a greater bending moment of inertia than the second portion;
 wherein the shaft includes a flexible portion connecting the shaft and the support formations to permit a displacement of the manipulation axis with respect to the support formations, the flexible portion consisting of a helical track extending about a circumference of the shaft; and
 wherein the shaft, the plurality of support formations and the flexible portion are integrally formed from a single tubular element.

2. The support device claim 1, wherein the tubular element is made of a shape memory material.

3. The support device of claim 1, wherein the support formations departing from a hub on the shaft are disposed adjacent to the connection portion.

4. The support device of claim 1, wherein the first portion of each support arm also extends in an axial direction from the distal portion of the shaft.

5. The support device of claim 1, wherein the flexible portion consists of a helical track extending at least three times around the shaft.

6. The support device of claim 1, further comprising a manipulation tool having a feature for releasably coupling with the coupling formation on the proximal end of the shaft and the manipulation tool having an ergonomic handle.

7. The support device of claim 1, wherein the shaft includes a plurality of through holes distributed and axially staggered around the shaft, such that each through hole is disposed at a position aligned with a corresponding supporting formation.

8. The support device of claim 7, wherein each of the through holes is disposed on the hub.

9. The support device of claim 1, wherein each support arm includes a first eyelet located at a position between the first and second portions and a second eyelet located at a free end of the second portion.

10. The support device of claim 1, wherein the stentless aortic heart valve prosthesis is coupled to the support device with suturing coupling each of the commissures of the stentless heart valve prosthesis to a corresponding support arm.

11. A support device for implantation of a stentless heart valve prosthesis having three leaflets adapted for coapting and defining three corresponding commissures, the support device including:
 a shaft defining a manipulation axis, the shaft having a proximal portion and a distal portion; and
 three support formations integrally formed and extending from the distal end of the shaft, the support formations disposed with even angular spacing around the manipulation axis of the shaft, such that each of the support formations correspond to locations of each of the commissures of the stentless heart valve prosthesis;
 wherein each of the support formations includes a first proximal portion extending from the distal end of the shaft with both a radial and an axial extension component, the axial extension component extending distally with respect to the shaft, the radial extension component extends radially away from the manipulation axis, and a second distal portion having a first end extending from the first proximal portion and having a second end that is free and that extends proximally with respect to the first end, the second distal portion extending parallel to the shaft and radially aligned with the first proximal portion, and the second distal portion of each support arm is bent with respect to the first proximal portion and extends proximally and parallel to the manipulation axis;

wherein the shaft includes a flexible portion connecting the shaft and the support formations to permit a displacement of the manipulation axis with respect to the support formations; and wherein the shaft, the plurality of support formations and the flexible portion are integrally formed from a single tubular element.

12. The support device of claim 11, wherein each of the first proximal portions has a first cross-sectional configuration and each of the second distal portions has a second cross-sectional configuration, the first cross-sectional configuration having a greater bending moment than the second cross-sectional configuration.

13. The support device of claim 12, wherein the first proximal portion has a U-shaped cross section.

14. The support device of claim 11, wherein each of the first proximal portions has a first dimension and each of the second distal portions has a second dimension, such that the first proximal portion has a greater bending stiffness than the second distal portion.

15. The support device of claim 11, further comprising a manipulation tool having a feature for releasably coupling with the coupling formation on the distal end of the shaft and the manipulation tool having an ergonomic handle.

16. The support device of claim 11, wherein the stentless aortic heart valve prosthesis is coupled to the support device with suturing coupling each of the commissures of the stentless heart valve prosthesis to a corresponding support arm.

17. The support device of claim 11, wherein the coupling formation is a helical track extending around a circumference of the shaft.

18. The support device of claim 17, wherein the helical track extends at least three times around the circumference of the shaft.

\* \* \* \* \*